(12) United States Patent
Vanpoucke

(10) Patent No.: US 8,914,125 B2
(45) Date of Patent: Dec. 16, 2014

(54) METHODS AND SYSTEMS FOR MINIMIZING AN EFFECT OF CHANNEL INTERACTION IN A COCHLEAR IMPLANT SYSTEM

(75) Inventor: Filiep J. Vanpoucke, Huldenberg (BE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 13/700,387

(22) PCT Filed: May 26, 2011

(86) PCT No.: PCT/US2011/038260
§ 371 (c)(1),
(2), (4) Date: Feb. 27, 2013

(87) PCT Pub. No.: WO2011/150292
PCT Pub. Date: Dec. 1, 2011

(65) Prior Publication Data
US 2013/0204326 A1    Aug. 8, 2013

Related U.S. Application Data

(60) Provisional application No. 61/349,667, filed on May 28, 2010.

(51) Int. Cl.
| A61N 1/32 | (2006.01) |
| A61N 1/05 | (2006.01) |
| A61N 1/36 | (2006.01) |
| H04R 25/00 | (2006.01) |

(52) U.S. Cl.
CPC ............ *A61N 1/36032* (2013.01); *A61N 1/323* (2013.01); *H04R 25/606* (2013.01); *A61N 1/0541* (2013.01)
USPC ............................................. 607/57; 607/137

(58) Field of Classification Search
USPC ........................................................ 607/57
See application file for complete search history.

(56) References Cited

U.S. PATENT DOCUMENTS

| 7,110,821 B1 | 9/2006 | Ross |
| 2006/0247735 A1* | 11/2006 | Honert ............................ 607/57 |
| 2007/0156202 A1 | 7/2007 | Zierhofer |

FOREIGN PATENT DOCUMENTS

WO    WO-2006/119069    11/2006

OTHER PUBLICATIONS

International Search Report and Written Opinion received in International Application No. PCT/US2011/038260 dated Nov. 18, 2011.

* cited by examiner

*Primary Examiner* — Carl H Layno
*Assistant Examiner* — Jon Eric C Morales
(74) *Attorney, Agent, or Firm* — ALG Intellectual Property, LLC

(57) ABSTRACT

An exemplary method of minimizing an effect of channel interaction among a plurality of channels in a multi-channel cochlear implant system includes empirically generating an electrical spread matrix that is specific to a patient and representative of a channel interaction among a plurality of channels defined by a plurality of electrodes of electrodes of a multi-channel cochlear implant system associated with the patient, generating a model electrical spread matrix that approximates the empirically generated electrical spread matrix and that has a band inverse matrix, and using the band inverse matrix to determine a set of stimulation current levels to be applied by way of a corresponding set of electrodes included in the plurality of electrodes in order to produce desired stimulation current levels at a plurality of stimulation sites within the cochlea in the presence of the channel interaction. Corresponding methods and systems are also disclosed.

19 Claims, 14 Drawing Sheets

700

702

| Z1,1 | Z1,2 | Z1,3 | Z1,4 | Z1,5 | Z1,6 | Z1,7 | Z1,8 |
| --- | --- | --- | --- | --- | --- | --- | --- |
| Z2,1 | Z2,2 | Z2,3 | Z2,4 | Z2,5 | Z2,6 | Z2,7 | Z2,8 |
| Z3,1 | Z3,2 | Z3,3 | Z3,4 | Z3,5 | Z3,6 | Z3,7 | Z3,8 |
| Z4,1 | Z4,2 | Z4,3 | Z4,4 | Z4,5 | Z4,6 | Z4,7 | Z4,8 |
| Z5,1 | Z5,2 | Z5,3 | Z5,4 | Z5,5 | Z5,6 | Z5,7 | Z5,8 |
| Z6,1 | Z6,2 | Z6,3 | Z6,4 | Z6,5 | Z6,6 | Z6,7 | Z6,8 |
| Z7,1 | Z7,2 | Z7,3 | Z7,4 | Z7,5 | Z7,6 | Z7,7 | Z7,8 |
| Z8,1 | Z8,2 | Z8,3 | Z8,4 | Z8,5 | Z8,6 | Z8,7 | Z8,8 |

$$\begin{bmatrix} r_{T1}^{-1} + r_{L1}^{-1} & -r_{L1}^{-1} & 0 & 0 \\ -r_{L1}^{-1} & r_{T2}^{-1} + r_{L1}^{-1} + r_{L1}^{-1} & -r_{L2}^{-1} & 0 \\ 0 & -r_{L2}^{-1} & r_{T3}^{-1} + r_{L2}^{-1} + r_{L3}^{-1} & -r_{L3}^{-1} \\ 0 & 0 & -r_{L3}^{-1} & r_{T4}^{-1} + r_{L3}^{-1} \end{bmatrix}$$

Fig. 11

METHODS AND SYSTEMS FOR MINIMIZING AN EFFECT OF CHANNEL INTERACTION IN A COCHLEAR IMPLANT SYSTEM

RELATED APPLICATIONS

The present application claims priority to U.S. Provisional Patent Application No. 61/349,667 by Filiep J. Vanpoucke, filed on May 28, 2010, and entitled "Methods and Systems for Minimizing an Effect of Channel Interaction in a Cochlear Implant System," the contents of which are hereby incorporated by reference in their entirety.

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant Systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

It is often desirable to simultaneously apply electrical stimulation to multiple stimulation sites within the cochlea by way of a plurality of electrodes. However, simultaneous stimulation may cause undesirable channel interaction among channels defined by the electrodes due to electrical current spread in the cochlear tissues. If the effect of such channel interaction could be minimized, the ability of a cochlear implant system to more effectively represent sound to a patient would be dramatically improved.

SUMMARY

An exemplary method of minimizing an effect of channel interaction among a plurality of channels in a multi-channel cochlear implant system includes empirically generating an electrical spread matrix that is specific to a patient and representative of a channel interaction among a plurality of channels defined by a plurality of electrodes of a multi-channel cochlear implant system associated with the patient, generating a model electrical spread matrix that approximates the empirically generated electrical spread matrix and that has a band (e.g., tridiagonal) inverse matrix, and using the band inverse matrix to determine a set of stimulation current levels to be applied by way of a corresponding set of electrodes included in the plurality of electrodes in order to produce desired stimulation current levels at a plurality of stimulation sites within the cochlea in the presence of the channel interaction.

An exemplary system for minimizing an effect of channel interaction among a plurality of channels in a multi-channel cochlear implant system includes an implantable cochlear stimulator configured to be implanted within a patient, a sound processor communicatively coupled to the implantable cochlear stimulator and configured to direct the implantable cochlear stimulator to generate and apply stimulation current to a plurality of stimulation sites within a cochlea of the patient by way of a plurality of electrodes disposed within the cochlea, and an interface device selectively and communicatively coupled to the sound processor. The interface device is configured to empirically generate an electrical spread matrix that is specific to the patient and representative of a channel interaction among a plurality of channels defined the plurality of electrodes, generate a model electrical spread matrix that approximates the empirically generated electrical spread matrix and that has a band (e.g., tridiagonal) inverse matrix, and direct the sound processor to use the band inverse matrix to determine a set of stimulation current levels to be applied by way of a corresponding set of electrodes included in the plurality of electrodes in order to produce desired stimulation current levels at at least one or more of the stimulation sites in the presence of the channel interaction.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 7 illustrates an exemplary electrical spread matrix that has been empirically derived according to principles described herein.

FIG. 11 illustrates an exemplary inverse matrix of a model electrical spread matrix according to principles described herein.

DETAILED DESCRIPTION

Methods and systems for minimizing an effect of channel interaction among a plurality of channels in a multi-channel cochlear implant system are disclosed herein. In some examples, an interface device may be selectively and communicatively coupled to the multi-channel cochlear implant system (e.g., to a sound processor included in the multi-channel cochlear implant system). The interface device may be configured to empirically generate an electrical spread matrix that is specific to the patient and representative of the channel interaction among the plurality of channels, generate a model electrical spread matrix that approximates the empirically generated electrical spread matrix, and use or direct the sound processor to use an inverse of the model electrical spread matrix to determine a set of stimulation current levels to be applied by way of a corresponding set of electrodes included in the plurality of electrodes in order to produce desired stimulation current levels at a plurality of stimulation sites within the cochlea in the presence of the channel interaction.

Numerous advantages are associated with the methods and systems described herein. For example, as will be described in more detail below, the inverse of the model electrical spread matrix is advantageously tridiagonal in its simplest embodiment (order 1), thus facilitating minimization of an effect of the channel interaction through the use of oblique and/or partial tripolar stimulation. In this manner, essentially independent stimulation channels may be realized, thereby increasing an ability of the multi-channel cochlear implant system to represent sound to a patient. Moreover, use of a tridiagonal inverse matrix is more computationally efficient and results in lower power consumption within the multi-channel cochlear implant system compared to alternative forms of reducing the effect of channel interaction.

As will be described in more detail below, the inverse of the model electrical spread matrix may be of any suitable order other than order 1 (i.e., tridiagonal). However, for illustrative purposes, it will be assumed that the inverse of the model electrical spread matrix is tridiagonal the examples provided herein.

Figure 1:
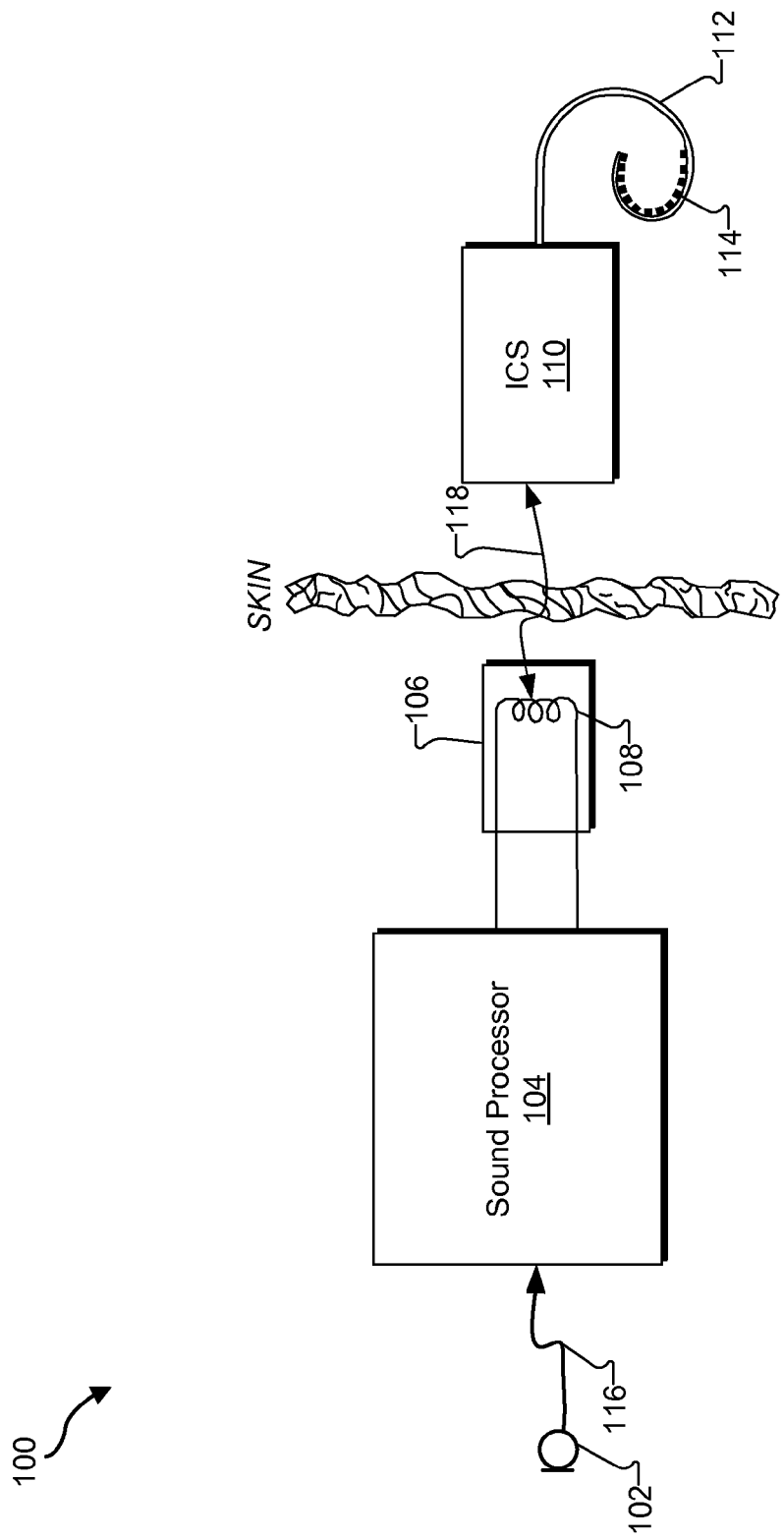
FIG. 1 illustrates an exemplary cochlear implant system according to principles described herein.

FIG. 1 illustrates an exemplary cochlear implant system 100. Cochlear implant system 100 may include a microphone 102, a sound processor 104, a headpiece 106 having a coil 108 disposed therein, an implantable cochlear stimulator ("ICS") 110, and a lead 112 with a plurality of electrodes 114 disposed thereon.

Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented within a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to implantable cochlear stimulator 110 with coil 108 by way of a communication link 118. These control parameters may be configured to specify one or more stimulation parameters, operating parameters, and/or any other parameter as may serve a particular implementation. Exemplary control parameters include, but are not limited to, stimulation current levels, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 120. It will be understood that data communication link 120 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processing device 102. Implantable cochlear stimulator 110 may be further configured to apply the electrical stimulation to one or more stimulation sites within the cochlea via one or more electrodes 114 disposed along lead 112. In some examples, implantable cochlear stimulator 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by implantable cochlear stimulator 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
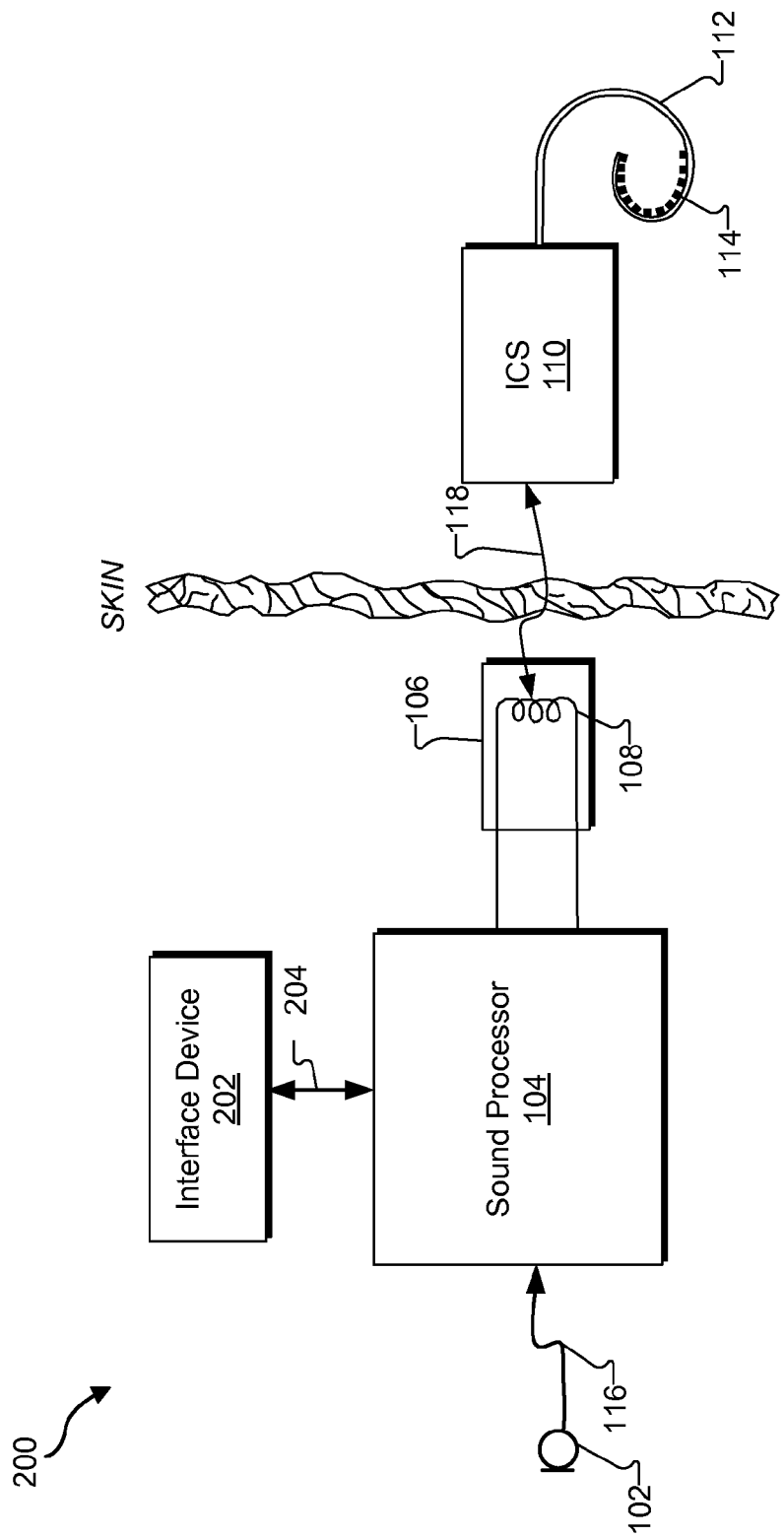
FIG. 2 illustrates an exemplary configuration wherein an interface device is selectively and communicatively coupled to a sound processor according to principles described herein.

FIG. 2 illustrates an exemplary configuration 200 wherein an interface device 202 is selectively and communicatively coupled to sound processor 104 by way of communication link 204. Interface device 202 may include any computing device or combination of computing devices configured to facilitate programming of one or more components of cochlear implant system 100. For example, interface device 202 may be used to fit cochlear implant system 100 to a patient.

Interface device 202 may include or be implemented by one or more fitting devices or stations, personal computers, handheld devices, mobile devices (e.g., a mobile phone), or any other suitable computing device. In some examples, interface device 202 may be used by a surgeon during or after an implantation procedure in which implantable cochlear stimulator 110 and/or lead 112 are implanted within the patient, a clinician (e.g., an audiologist), and/or other users as may serve a particular implementation.

In some examples, interface device 202 may be configured to facilitate empirical generation of an electrical spread matrix that is specific to a patient and representative of a channel interaction among a plurality of channels defined by electrodes 114. An exemplary process that may be used to generate the electrical spread matrix will be described in more detail below.

Interface device 202 may be further configured to generate a model electrical spread matrix that approximates the empirically generated electrical spread matrix. As will be described in more detail below, the model electrical spread matrix may be associated with a ladder network model of the cochlea. The ladder network may include a plurality of segments each including a longitudinal resistor representative of current flow between adjacent electrodes and a transversal resistor representative of current that exits the cochlea to return to a reference electrode disposed outside the cochlea. As will also be described in more detail below, the model electrical spread matrix may advantageously have a tridiagonal (or other suitable order) inverse matrix, which may be used to determine a set of stimulation current levels to be applied by way of a corresponding set of electrodes included in electrodes 114 in order to produce desired stimulation current levels at a plurality of stimulation sites within the cochlea in the presence of channel interaction.

Figure 3:
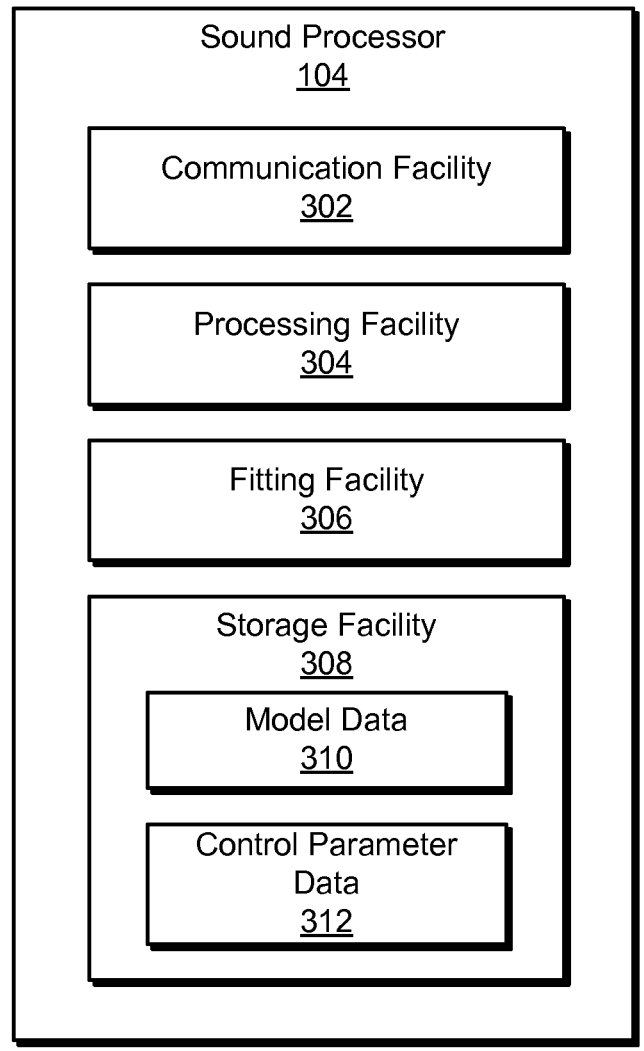
FIG. 3 illustrates exemplary components of a sound processor according to principles described herein.

FIG. 3 illustrates exemplary components of sound processor 104. As shown in FIG. 3, sound processor 104 may include a communication facility 302, a processing facility 304, a fitting facility 306, and a storage facility 308, any or all of which may be in communication with one another using any suitable communication technologies. Each of these facilities will now be described in more detail.

Communication facility 302 may be configured to facilitate communication between sound processor 104 and implantable cochlear stimulator 110. For example, communication facility 302 may include transceiver components configured to wirelessly transmit data (e.g., control parameters and/or power signals) to implantable cochlear stimulator 110 and/or wirelessly receive data (e.g., current, voltage, and/or impedance measurement data) from implantable cochlear stimulator 110 by way of communication link 118. Communication facility 302 may be further configured to facilitate communication between sound processor 104 and interface device 202. For example, communication facility 302 may be configured to receive model data from interface device 202 and/or transmit model data to interfaced device 202 by way of communication link 204.

Processing facility 304 may be configured to perform one or more signal processing heuristics on an audio signal presented to the patient. For example, processing facility 304 may perform one or more pre-processing operations, spectral analysis operations, noise reduction operations, mapping operations, and/or any other types of signal processing operations on a detected audio signal as may serve a particular implementation. In some examples, processing facility 304 may generate one or more control parameters governing an operation of implantable cochlear stimulator 110 (e.g., one or more stimulation parameters defining the electrical stimulation to be generated and applied by implantable cochlear stimulator 110).

Fitting facility 306 may be configured to fit implantable cochlear stimulator 110 to a patient in accordance with strain data detected by strain gauge assembly 116. As used herein, "fitting" implantable cochlear stimulator 110 to a patient refers to adjusting (i.e., optimizing) one or more control parameters governing an operation of implantable cochlear stimulator 110 or otherwise programming implantable cochlear stimulator 110 to meet the specific needs of the patient. For example, fitting facility 306 may be configured to utilize model data provided by interface device 202 to determine appropriate stimulation current levels to be applied by way of one or more of electrodes 114.

The fitting may be performed by fitting facility 306 at any suitable time as may serve a particular implementation. For example, fitting facility 306 may fit implantable cochlear stimulator 110 to a patient during an initial fitting procedure that occurs soon after implantable cochlear stimulator 110 is implanted within the patient and/or at any subsequent time as may serve a particular implementation.

In some examples, fitting facility 306 may be configured to automatically perform a fitting procedure without input provided by a surgeon, clinician, or other user. Additionally or alternatively, fitting facility 306 may be configured to perform a fitting procedure in response to input provided by a user.

Storage facility 308 may be configured to maintain model data 310 representative of data associated with a modeling of the cochlea (e.g., data representative of a model electrical spread matrix) and control parameter data 312 representative of one or more control parameters generated by processing facility 304. Storage facility 308 may be configured to maintain additional or alternative data as may serve a particular implementation.

Figure 4:
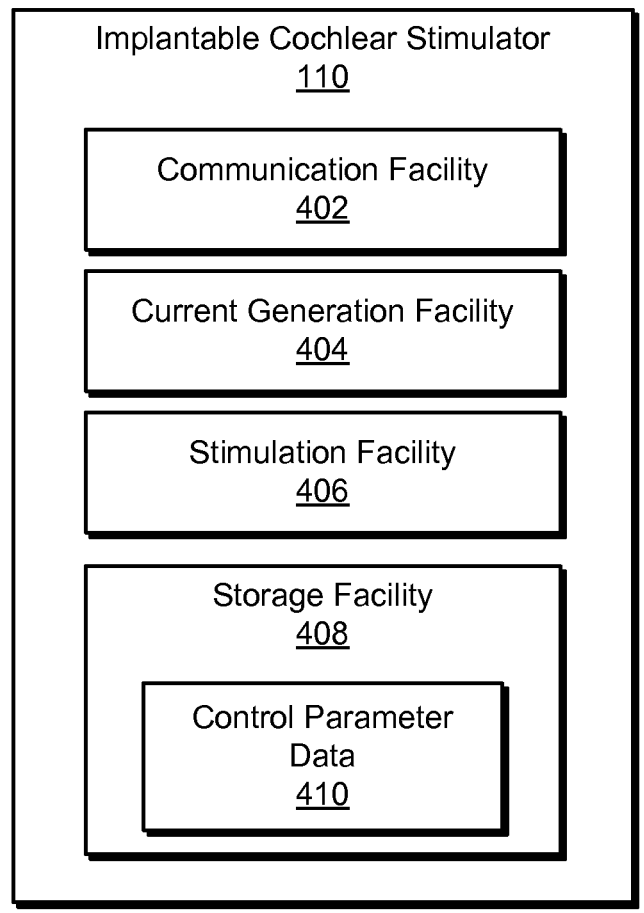
FIG. 4 illustrates exemplary components of an implantable cochlear stimulator according to principles described herein.

FIG. 4 illustrates exemplary components of implantable cochlear stimulator 110. As shown in FIG. 4, implantable cochlear stimulator 110 may include a communication facility 402, a current generation facility 404, a stimulation facility 406, and a storage facility 408, any or all of which may be in communication with one another using any suitable communication technologies. Each of these facilities will now be described in more detail.

Communication facility 402 may be configured to facilitate communication between implantable cochlear stimulator 110 and sound processor 104. For example, communication facility 402 may include one or more coils configured to receive control signals and/or power via one or more communication links to implantable cochlear stimulator 110. Communication facility 402 may additionally or alternatively be configured to transmit one or more status signals and/or other data to sound processor 104. Communication facility 402 may be further configured to facilitate communication between implantable cochlear stimulator 110 and any other externally located device (e.g., interface device 202).

Current generation facility 404 may be configured to generate stimulation current in accordance with one or more stimulation parameters received from sound processor 104. To this end, current generation facility 404 may include one or more current sources and/or any other circuitry configured to generate stimulation current. For example, current generation facility 404 may include an array of independent current sources each corresponding to a distinct channel defined by one or more electrodes 114.

Stimulation facility 406 may be configured to facilitate application of the stimulation current generated by current generation facility 404 to one or more stimulation sites within the patient in accordance with one or more stimulation parameters received from sound processor 104. To this end, stimulation facility 406 may be configured to interface with one or more of electrodes 114.

Storage facility 408 may be configured to maintain control parameter data 410 as received from sound processor 104. Control parameter data 410 may be representative of one or more control parameters configured to govern one or more operations of implantable cochlear stimulator 110. For example, control parameters data 410 may include data representative of one or more stimulation parameters configured to define the electrical stimulation generated and applied by implantable cochlear stimulator 110. Storage facility 408 may be configured to maintain additional or alternative data as may serve a particular implementation.

Figure 5:
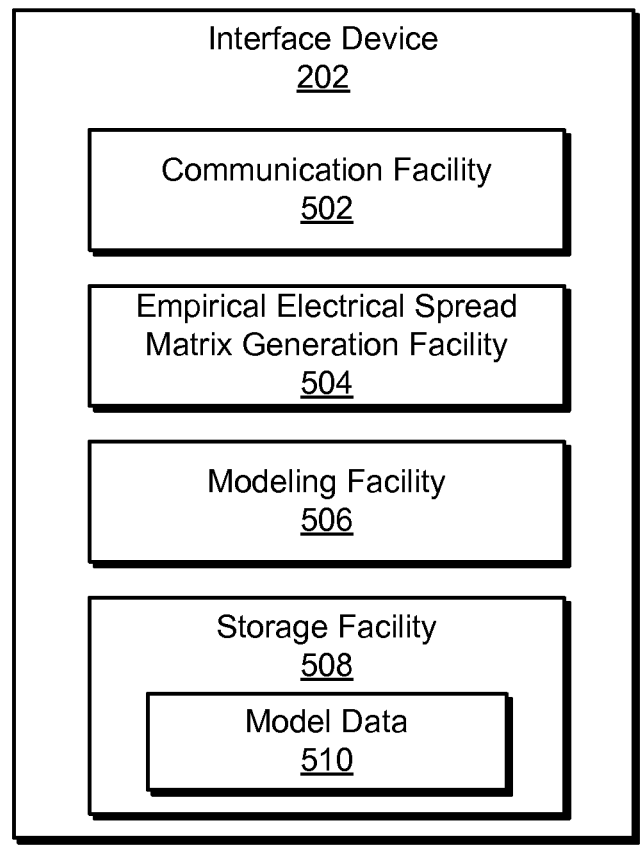
FIG. 5 illustrates exemplary components of an interface device according to principles described herein.

FIG. 5 illustrates exemplary components of interface device 202. As shown in FIG. 5, interface device 202 may include a communication facility 502, an empirical electrical spread matrix generation facility 504, a modeling facility 506, and a storage facility 508, any or all of which may be in communication with one another using any suitable communication technologies. Each of these facilities will now be described in more detail.

Communication facility 502 may be configured to facilitate communication between interface device 202 and sound processor 104. For example, communication facility 502 may include transceiver components configured to wirelessly transmit data (e.g., model data) to sound processor 104 and/or wirelessly receive data (e.g., feedback data, impedance measurement data, neural response data, etc.) from sound processor 104 by way of communication link 204. In some examples, communication facility 502 may be further configured to facilitate communication between interface device 202 and implantable cochlear stimulator 110.

Empirical electrical spread matrix generation facility 504 may be configured to empirically generate an electrical spread matrix representative of a channel interaction among the channels defined by electrodes 114. Exemplary manners in which the electrical spread matrix may be empirically generated will be described in more detail below.

Modeling facility 506 may be configured to generate a model electrical spread matrix that approximates the empirically generated electrical spread matrix. To this end, modeling facility 506 may model a current spread through tissues of the cochlea as a ladder network (also referred to as a "leaky transmission line") comprising a plurality of segments that each include a longitudinal resistor representative of current flow between adjacent electrodes and a transversal resistor representative of current that exits the cochlea to return to a reference electrode disposed outside the cochlea. As will be described below, the ladder network may be extended with longitudinal resistors of higher order.

In some examples, modeling facility 506 may be configured to determine values for each longitudinal resistor and each transversal resistor that result in the model electrical spread matrix optimally matching the empirically generated electrical spread matrix. The resistor value determination may be performed according to any suitable heuristic, as will be described in more detail.

Modeling facility 506 may be further configured to determine the inverse of the model electrical spread matrix. The inverse matrix may be provided to sound processor 104, which may use the inverse matrix to determine a set of stimulation levels to be applied by way of a corresponding set of electrodes (which may be less than or equal to the total number of electrodes 114) in order to produce desired stimulation current levels at a plurality of stimulation sites within the cochlea in the presence of the channel interaction.

Storage facility 508 may be configured to maintain model data 510 representative of data associated with a modeling of the cochlea (e.g., data representative of a model electrical spread matrix, an inverse of the model electrical spread matrix, longitudinal and transversal resistor values, etc.). Storage facility 508 may be configured to maintain additional or alternative data as may serve a particular implementation.

Figure 6:
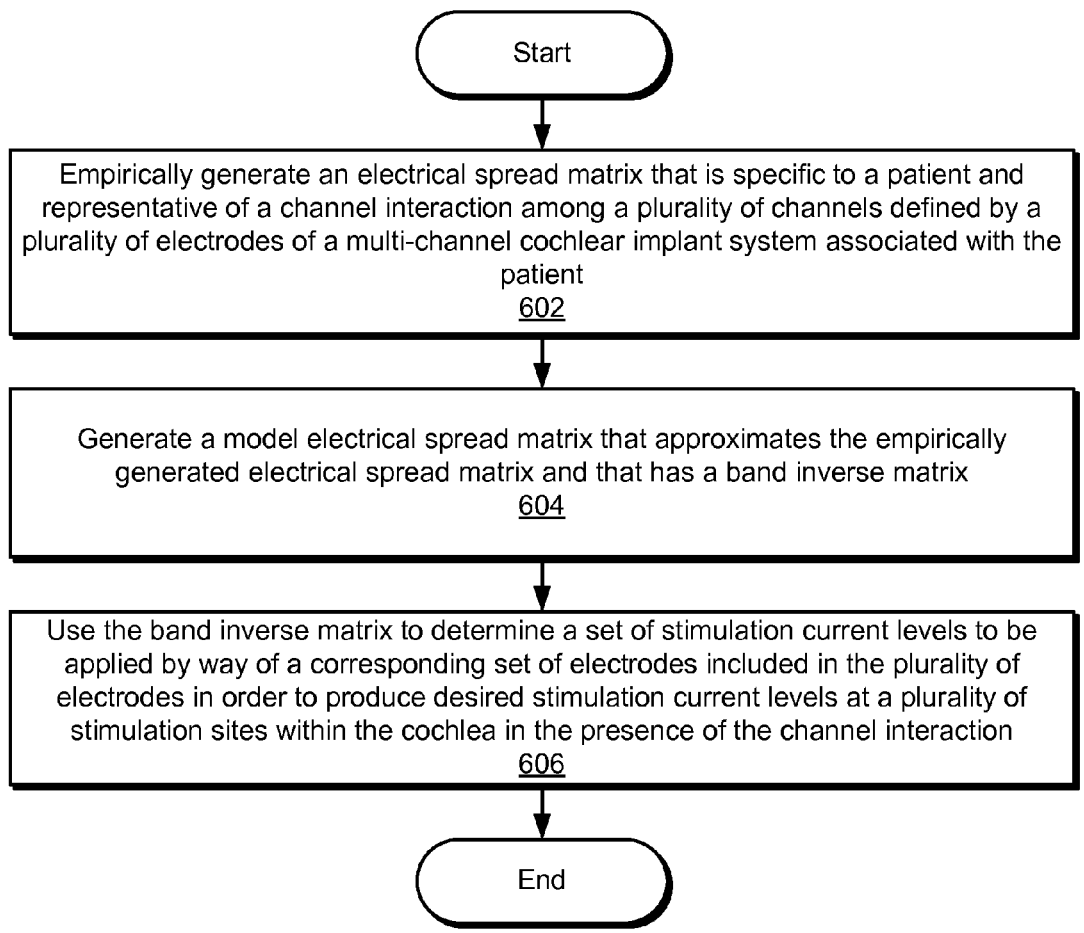
FIG. 6 illustrates an exemplary method of minimizing an effect of channel interaction in a cochlear implant system according to principles described herein.

FIG. 6 illustrates an exemplary method 600 of minimizing an effect of channel interaction in a cochlear implant system (e.g., cochlear implant system 100). While FIG. 6 illustrates exemplary steps according to one embodiment, other embodiments may omit, add to, reorder, and/or modify any of the steps shown in FIG. 6. One or more steps shown in FIG. 6 may be performed by any suitable computing device. For example, one or more steps shown in FIG. 6 may be performed by one or more components of interface device 202 and/or sound processor 104.

In step 602, an electrical spread matrix is empirically generated. The electrical spread matrix is specific to a patient and representative of a channel interaction among a plurality of channels defined by a plurality of electrodes of a multi-channel cochlear implant system associated with the patient.

The electrical spread matrix may be empirically generated using any suitable heuristic. For example, an electrical field imaging ("EFI") heuristic may be used to generate the electrical spread matrix. To illustrate, interface device 202 may direct implantable cochlear stimulator 110 (by way of sound processor 104) to apply a known stimulation current to each electrode included in the plurality of electrodes 114. Each time the known stimulation current is applied to one of the electrodes, an intracochlear potential is measured at each of the plurality of electrodes (including the stimulating electrode). The measured potentials may be divided by the known stimulation current for normalization purposes. The normalized potentials have, therefore, Ohm units, and may be represented by impedance values that define the relation between the injected current at one electrode and induced potential at another. Note that the measurements taken on the electrodes include a contact impedance contribution, and therefore do not represent the voltage in the cochlear tissue. Hence, they may be postprocessed (e.g., by interpolating the impedances on the neighboring contacts). Alternatively, the electrical spread matrix may be generated using a neural response imaging heuristic, a mathematical simulation of electrical volume conduction, one or more psycho-acoustic methods, and/or any other heuristic as may serve a particular implementation.

The empirically derived impedance values may be included within an electrical spread matrix, which may be represented herein by Z. An electrical spread matrix may alternatively be referred to as a channel interaction matrix, an impedance matrix, or an EFI matrix. FIG. 7 illustrates an exemplary electrical spread matrix 700 that may be empirically derived based on an array of eight electrodes that define eight distinct channels by which stimulation current may be applied to corresponding stimulation sites within the cochlea. Because electrical spread matrix 700 is based on an array of eight electrodes, electrical spread matrix 700 is eight by eight. It will be recognized electrical spread matrix 700 may alternately be based on any other number of electrodes (e.g., sixteen) and therefore have a correspondingly different size (e.g., sixteen by sixteen).

In general, the channel interaction at any electrode Ej (j=1–8) resulting from application of a current of known magnitude to electrode Ei (i=1–8) may be expressed within electrical spread matrix 700 as Zi,j=Vj/Ii. For example, as shown in cell 702, the channel interaction of a second electrode within the electrode array that results from application of current to a first electrode within the electrode array may be expressed as Z1,2.

In some examples, the empirically derived electrical spread matrix may be used to determine a voltage that should appear on each electrode if a desired stimulation current were applied to the electrode. The voltage that will appear in the cochlea when multiple electrodes are simultaneously stimulated is given by Equation 1:

$$V = Z * I \quad \text{(Equation 1).}$$

In Equation 1, Z represents the empirically generated electrical spread matrix, I represents a vector of the simultaneously applied stimulation current levels applied to each of the electrodes, and V represents a vector of the voltages that appear in a vicinity of each electrode as a result of the stimulation current levels being applied to each of the electrodes. The voltage in the cochlea is therefore a linear combination of all the contributions of the individual electrodes. In a typical cochlear implant sound processing scheme, the stimulation current vector I represent the spectral information to be delivered to the auditory nerve. The voltage profile V is only a faithful representation of the current profile I if the matrix Z is diagonal, i.e. no smoothing occurs. In reality, Z is not diagonal. Therefore, in the standard cochlear implant scheme all channels are stimulated sequentially.

It is possible however to compensate for the channel interaction effect by compensating the electrical currents. In Equation 2 shown below, the stimulation currents are modified to multiplying the original stimulation currents with a diagonal matrix D (scaling factor representative of the cochlear tissue impedance) and the inverse of the electrical spread matrix:

$$I_r = Z^{-1} * D * I \quad \text{(Equation 2).}$$

In Equation 2, $Z^{-1}$ represents an inverse matrix of the electrical spread matrix Z and $I_r$ represents a vector of the set of required stimulation current levels that will produce the desired voltage in the cochlea. The inverse matrix may also be referred to as an admittance matrix Y. Equations 1 and 2 may be combined to yield:

$$V = (Z * Z^{-1}) * (D * I) \quad \text{(Equation 3).}$$

As shown in Equation 2, the required stimulation current levels $I_r$ may be determined using the inverse of the empirically generated electrical spread matrix Z.

However, $Z^{-1}$ and Z are typically both full matrices. In other words, each entry within $Z^{-1}$ and Z is non-zero. Hence, Equation 3 requires a stimulation current to be concurrently applied to each electrode within the electrode array in order to compensate for channel interaction. Such concurrent stimulation by way of each electrode included within the electrode array may be computationally inefficient and consume an undesirable amount of batter power. Moreover, numerical instability may result in overly loud stimulation by a cochlear implant system.

Hence, the methods and systems described herein do not use the inverse of the empirically generated electrical spread matrix (i.e., $Z^{-1}$) to determine the required stimulation current levels $I_r$. Rather, as will be described in more detail below, the inverse of a model electrical spread matrix that approximates the empirically generated electrical spread matrix may be used to determine the required stimulation current levels $I_r$. This inverse matrix is a band matrix (e.g., tridiagonal), which, as will be described in more detail below, minimizes the number of electrodes by which electrical stimulation current must be applied in order to minimize an effect of channel interaction in a cochlear implant system.

Returning to FIG. 6, in step 604, a model electrical spread matrix that approximates the empirically generated electrical spread matrix and that has a tridiagonal inverse matrix is generated. To this end, the computing device (e.g., interface device 202) may model a current spread through tissues of the cochlea as a ladder network (or leaky transmission line) comprising a plurality of segments that each include a longitudinal resistor representative of current flow between adjacent electrodes and a transversal resistor representative of current that exits the cochlea to return to a reference electrode disposed outside the cochlea.

Figure 8:
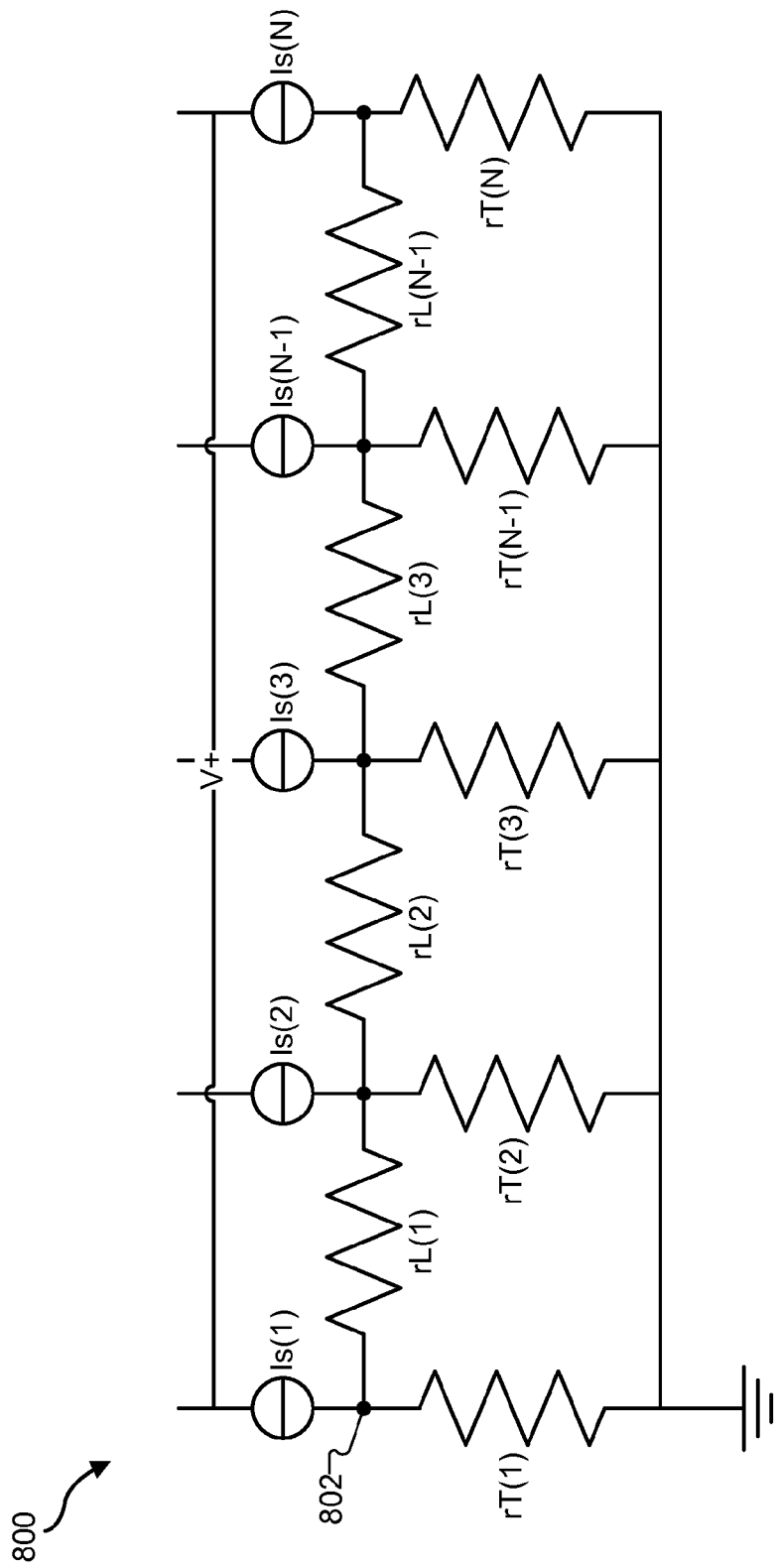
FIG. 8 illustrates an exemplary ladder network model that may used to model current spread through tissues of the cochlea according to principles described herein.

FIG. 8 illustrates an exemplary ladder network model 800 that may used to model current spread through tissues of the cochlea. As shown in FIG. 8, ladder network model 800 may include a plurality of segments each including a transversal resistor (e.g., resistor rT(1)), a longitudinal resistor (e.g., resistor rL(1)), and a current source (e.g., Is(1)). Each transversal resistor is representative of current that exits the cochlea to return to a reference electrode disposed outside the cochlea. Each longitudinal resistor is representative of current flow between adjacent electrodes. Each segment further includes a single node (e.g., node 802) modeling a voltage potential at each of the electrodes.

Figure 9:
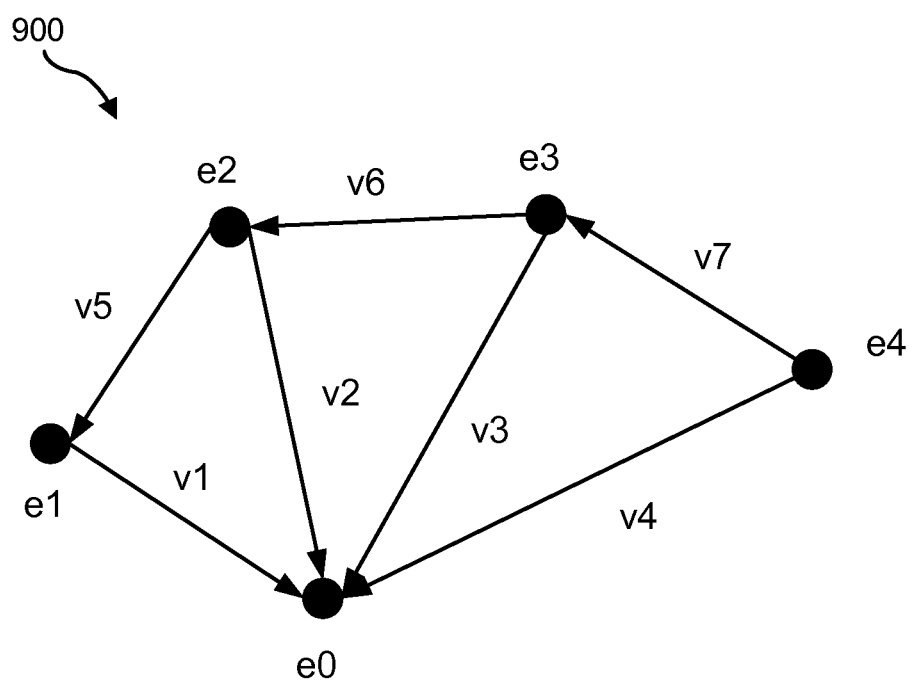
FIG. 9 shows an exemplary network topology according to principles described herein.

In some examples, a topology matrix A (also referred to as an incidence matrix) may be used to describe a topology or interconnectivity of a ladder network model (e.g., ladder network model 800). To illustrate, FIG. 9 shows an exemplary network topology 900 that may be associated with a particular electrode array that includes four intracochlear electrodes e1 through e3. Electrode e0 represents a return electrode or ground that is disposed outside the cochlea. Hence, as shown in FIG. 9, network topology 900 may include five nodes and seven branches interconnecting the nodes. Each node is labeled e0 through e4 and each branch is labeled v1 through v7.

Figure 10:
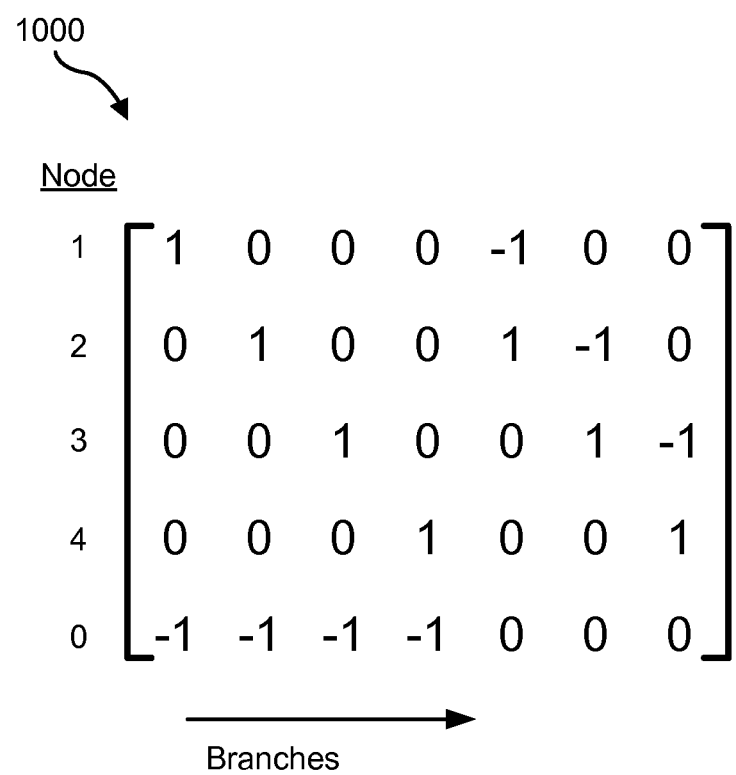
FIG. 10 shows a topology matrix corresponding to the exemplary network topology of FIG. 9 according to principles described herein.

FIG. 10 shows a topology matrix 1000 corresponding to the exemplary network topology 900 of FIG. 9. As shown in FIG. 10, each entry within topology matrix 1000 may be 1, −1, or 0. A "1" represents a flow of current away from a node by way of the corresponding branch, a "1" represents a flow of current into the node by way of the corresponding branch, and a "0" indicates that current does not flow to or away from the node by way of the corresponding branch. For example, the first row of topology matrix 900 indicates that current flows away from the first node by way of the branch labeled v1 and that current flows towards the first node by way of the branch labeled v5.

The topology matrix A may be used to determine the model electrical spread matrix and/or the inverse of the model electrical spread matrix. For example, consider the following equations:

$$A * i = i_s \quad \text{(Equation 4);}$$

$$A^T * e = v \quad \text{(Equation 5); and}$$

$$i = R^{-1} * v \quad \text{(Equation 6).}$$

In Equation 4, i is a vector representing the current in each branch of ladder network model 800 and $i_s$ is a vector representative of the stimulation current provided by each of the current sources Is(1) through Is(N) shown in FIG. 8. Equation 4 has been derived in accordance with Kirchhoff's current law, which states that the sum of all currents in a node equals zero. In Equation 5, $A^T$ is a matrix representative of the transpose of topology matrix A, e is a vector representative of a voltage at each of the nodes shown in FIG. 8, and v is a vector representative of the branch voltages associated with each branch in FIG. 8. Equation 5 has been derived in accordance with Kirchhoff's voltage law, which states that in all closed loops, the sum of the branch voltages is zero. Finally, in Equation 6, R is a diagonal matrix containing the conductivities of the branches shown in FIG. 8. Equation 6 has been derived in accordance with Ohm's law and states that i is equal to the inverse of the diagonal of R multiplied by v. Because e=Z*I (Ohm's law), Equations 4, 5, and 6 may be combined to yield:

$$Z_m^{-1} = A * R^{-1} * A^T \quad \text{(Equation 7).}$$

Hence, Equation 7 may be used to determine the inverse of the model electrical spread matrix $Z_m$ (i.e., $Z_m^{-1}$). The inverse matrix $Z_m^{-1}$ may also be referred to as an admittance matrix $Y_m$ and is tridiagonal in structure. In other words, the inverse matrix has nonzero elements only in the main diagonal, the first diagonal below the main diagonal, and the first diagonal above the main diagonal.

FIG. 11 illustrates an exemplary inverse matrix 1100 of a model electrical spread matrix. As shown in FIG. 11, the nonzero elements of inverse matrix 1100 are based on longitudinal and transversal resistor values included in the ladder network model 800 of FIG. 8. For example, the first element of inverse matrix 1100 is equal to $r_{T1}^{-1} + r_{L1}^{-1}$. The other elements of inverse matrix 1100 are as shown in FIG. 11. Note that the matrix is symmetric, but that the values on a diagonal line are not necessarily identical.

In some examples, the generating of the model electrical spread matrix as described in step 604 of FIG. 6 includes determining values for each longitudinal resistor and each transversal resistor that result in the model electrical spread matrix optimally matching the electrical spread matrix empirically generated in step 602. The resistor value determination may be performed according to any suitable optimization heuristic (e.g., steepest descent, etc.).

To illustrate, the resistor values may be determined in accordance with Equation 8:

$$\min_{r_T, r_L} \|Z - Z_m(r_T, r_L)\|_{OFF} \quad \text{(Equation 8).}$$

The operator $\|X\|_{OFF} = \Sigma_k \Sigma_{l \neq k} X[k,l]^2$ denotes the norm of the off-diagonal elements of the matrix. This is done in order to exclude the diagonal elements of Z as these values are also affected by the electrode impedances.

In some examples, the resistor values may be determined such that the model electrical spread matrix $Z_m$ approximates the empirically generated electrical spread matrix Z with a relatively high amount of accuracy (e.g., 95 percent or higher). Hence, using the inverse of the model electrical spread matrix (i.e., $Z_m^{-1}$) to determine the required set of stimulation levels to produce desired stimulation current levels at a plurality of stimulation sites may be practically as effective as using the inverse of the empirically generated electrical spread matrix (i.e., $Z^{-1}$).

In some alternative examples, the resistor values may be determined using the inverse matrix $Z_m^{-1}$. The optimization problem may computationally more elegant when using the inverse matrix $Z_m^{-1}$ as it has the standard structure of a set of linear equations.

In step 606 of FIG. 6, the tridiagonal inverse matrix $Z_m^{-1}$ is used to determine a set of stimulation current levels to be applied by way of a corresponding set of electrodes included in the plurality of electrodes in order to produce desired stimulation current levels at a plurality of stimulation sites within the cochlea in the presence of the channel interaction. For example, the set of stimulation current levels may be determined in accordance with Equation 9:

$$I_r = Z_m^{-1} * (D * I_d) \quad \text{(Equation 9).}$$

In Equation 9, D represents a diagonal matrix with the diagonal values of the empirically generated electrical spread matrix Z, $I_d$ represents a matrix of the desired stimulation current levels to be applied to each of the electrodes, and $I_r$ represents a matrix of the set of required stimulation current levels that will produce the desired stimulation current levels $I_d$. Because $Z_m^{-1}$ is tridiagonal, the effect of channel interaction may be minimized using up to three electrodes per channel (i.e., oblique and/or partial tripolar stimulation) by which desired stimulation current is to be produced. Such tripolar stimulation is computationally more efficient and less resource intensive than simultaneous stimulation that uses all of the electrodes in an electrode array.

Figure 12:
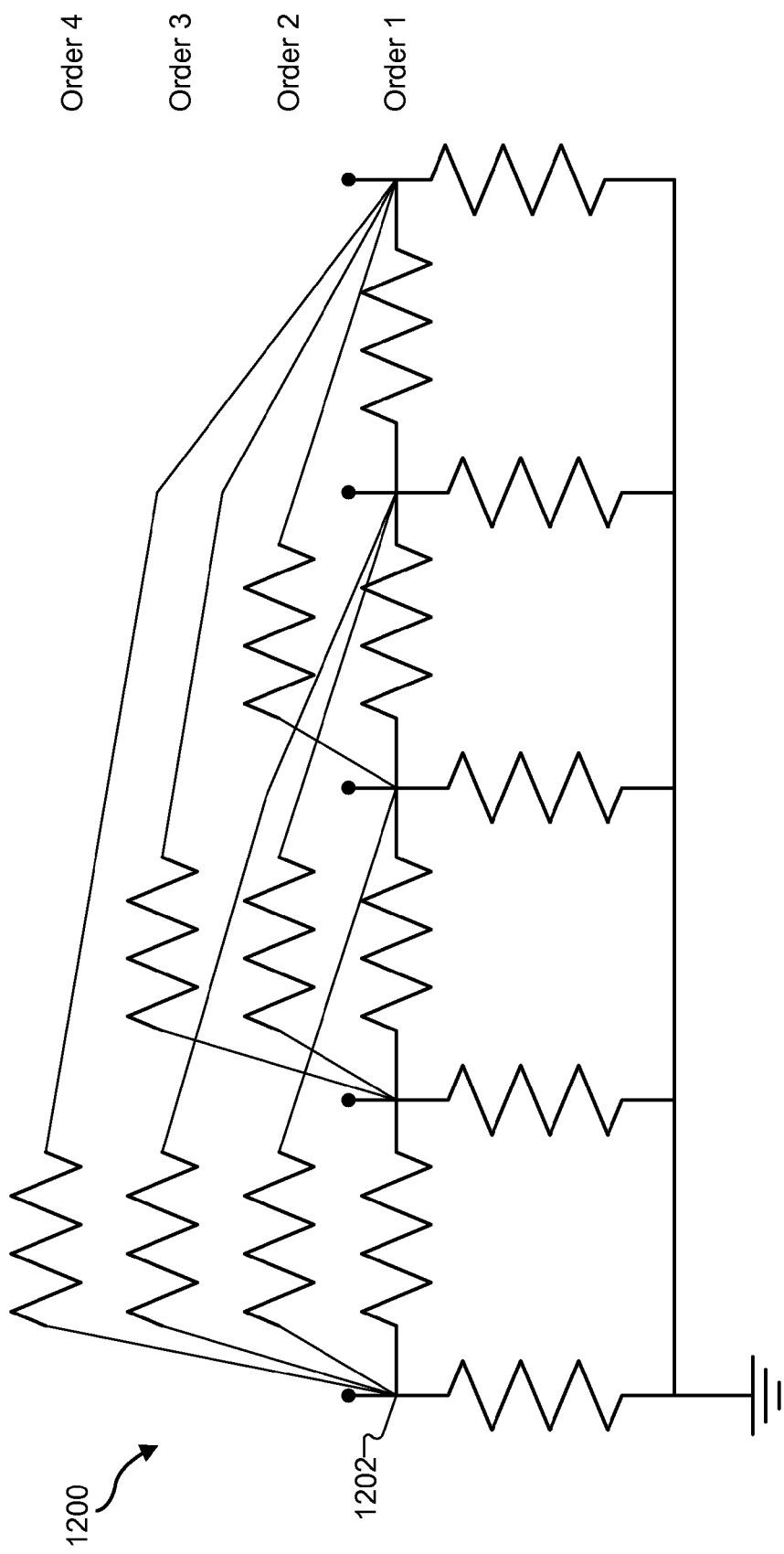
FIG. 12 illustrates an exemplary ladder network model that may used to model current spread through tissues of the cochlea according to principles described herein.

FIG. 12 illustrates an exemplary ladder network model 1200 that may be used to model current spread through tissues of the cochlea. Ladder network model 1200 is of higher order than that of ladder model network 800 in that it has additional longitudinal resistors of longer length that connect to electrodes at longer distances. The order may be defined as the biggest inter-electrode distance spanned by a longitudinal resistor. If the order equals the number of electrodes minus one, then it is at "full order."

In some examples, the additional degrees of freedom associated with higher order ladder network model 1200 allow for modeling the empirical electrical spread matrix more accurately. The mathematical effect on the inverse matrix of adding these layers of longer longitudinal resistors is that the inverse matrix is no longer tridiagonal, but has also non-zero entries in diagonals at a distance of two and higher of the main diagonal. This may result in a family of patient-specific spatial filters that are spatially more and more selective as the order grows.

Figure 13:
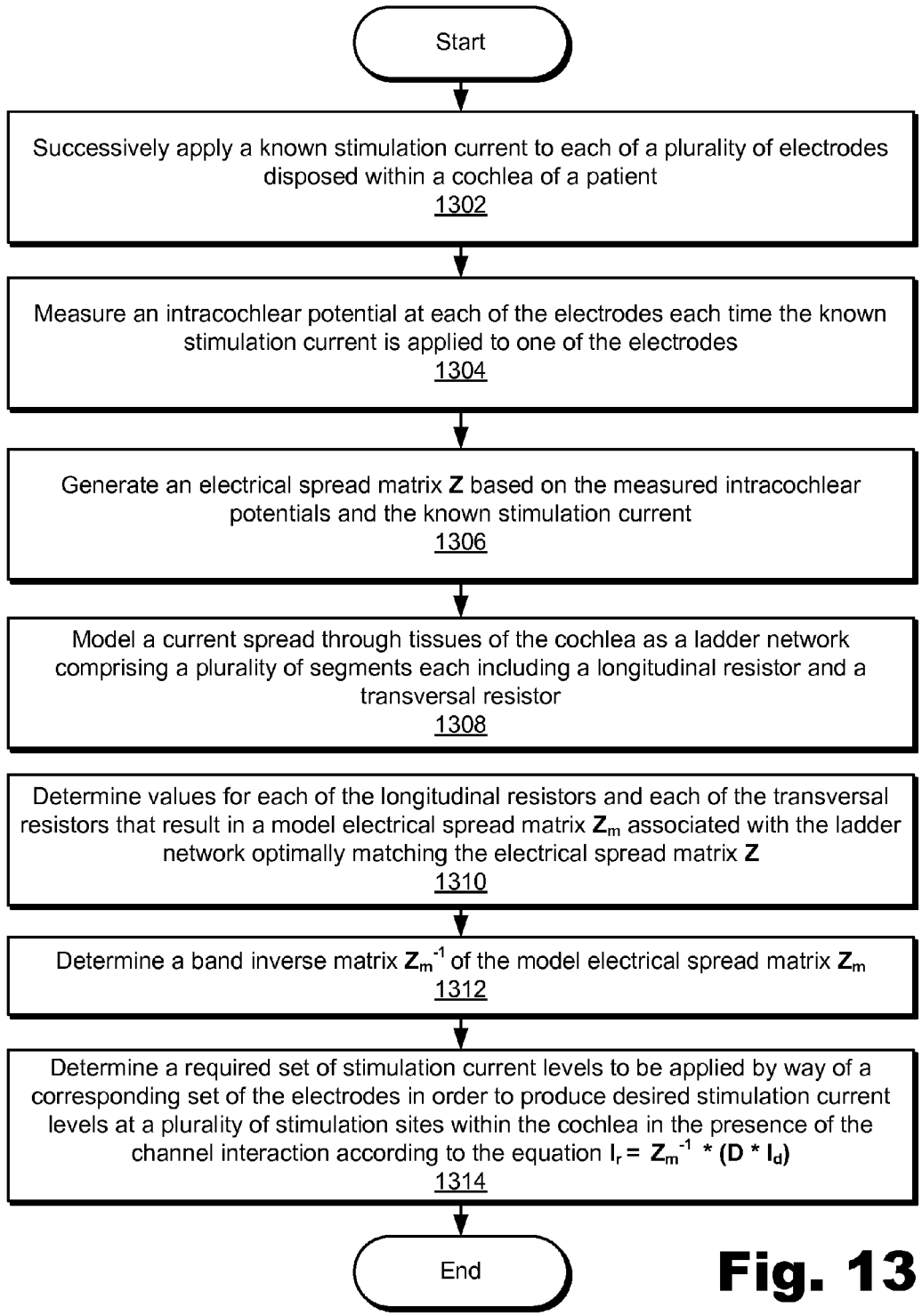
FIG. 13 illustrates another exemplary method of minimizing an effect of channel interaction in a cochlear implant system according to principles described herein.

FIG. 13 illustrates another exemplary method 1300 of minimizing an effect of channel interaction in a cochlear implant system (e.g., cochlear implant system 100). While FIG. 13 illustrates exemplary steps according to one embodiment, other embodiments may omit, add to, reorder, and/or modify any of the steps shown in FIG.

13. One or more steps shown in FIG. 13 may be performed by any suitable computing device. For example, one or more steps shown in FIG. 13 may be performed by one or more components of interface device 202 and/or sound processor 104. Moreover, each of the steps illustrated in FIG. 13 may be performed in any of the ways described herein.

In step 1302, a known stimulation current is successively applied to each of a plurality of electrode disposed within a cochlea of a patient.

In step 1304, an intracochlear potential is measured at each of the electrodes each time the known stimulation current is applied to one of the electrodes.

In step 1306, an electrical spread matrix Z based on the measured intracochlear potentials and the known stimulation current is generated.

In step 1308, a current spread through tissues of the cochlea is modeled as a ladder network comprising a plurality of segments each including a longitudinal resistor and a transversal resistor.

In step 1310, values for each of the longitudinal resistors and each of the transversal resistors are determined that result in a model electrical spread matrix $Z_m$ associated with the ladder network optimally matching the electrical spread matrix Z.

In step 1312, a tridiagonal inverse matrix $Z_m^{-1}$ of the model electrical spread matrix $Z_m$ is determined. Steps 1302 through 1212 may be performed once in time, e.g., during an initial fitting session with a patient, as the electrical spread matrix remains stable over time.

In step 1314, during standard operation of the cochlear implant system, a required set of stimulation current levels to be applied by way of a corresponding set of the electrodes in order to produce desired stimulation current levels at a plurality of stimulation sites within the cochlea in the presence of the channel interaction is determined according to the equation $I_r = Z_m^{-1} * (D * I_d)$. Each of these matrices is described in more detail above.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 14:
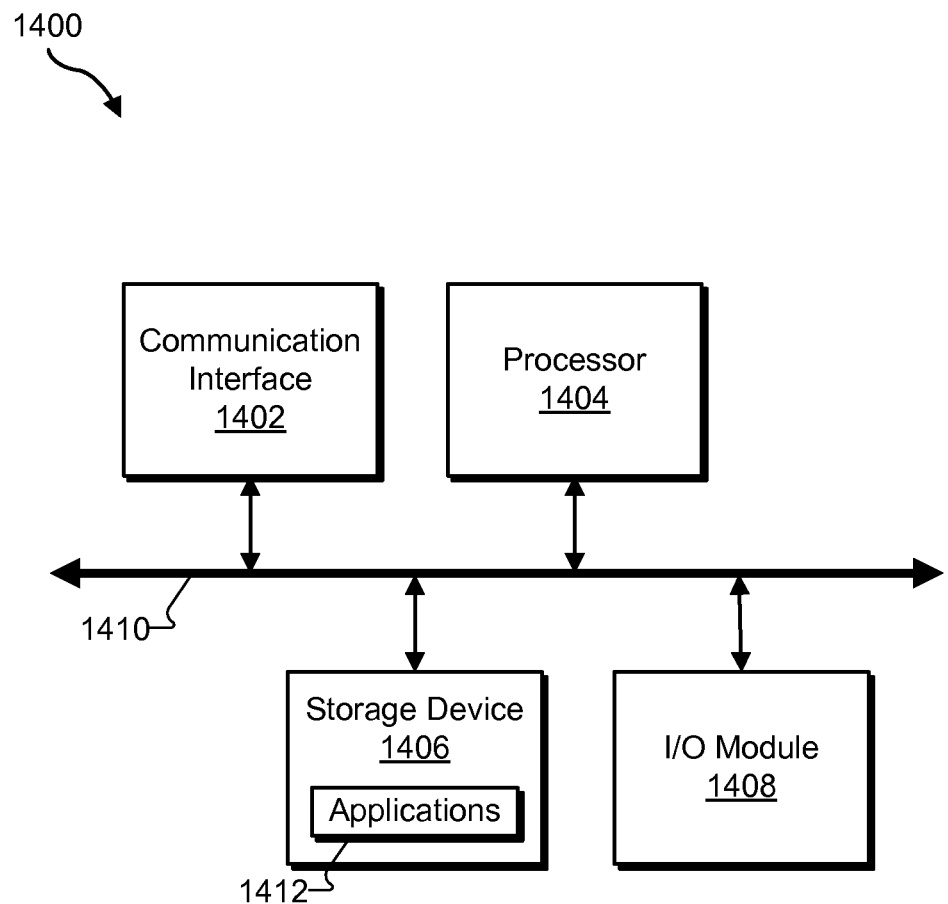
FIG. 14 illustrates an exemplary computing device according to principles described herein.

FIG. 14 illustrates an exemplary computing device 1400 that may be configured to perform one or more of the processes described herein. As shown in FIG. 14, computing device 1400 may include a communication interface 1402, a processor 1404, a storage device 1406, and an input/output ("I/O") module 1408 communicatively connected via a communication infrastructure 1410. While an exemplary computing device 1400 is shown in FIG. 14, the components illustrated in FIG. 14 are not intended to be limiting. Additional or alternative components may be used in other embodiments. Components of computing device 1400 shown in FIG. 14 will now be described in additional detail.

Communication interface 1402 may be configured to communicate with one or more computing devices. Examples of communication interface 1402 include, without limitation, a wired interface, a wireless interface, and/or any other suitable interface. Communication interface 1402 may be configured to interface with any suitable communication media, protocols, and formats, including any of those mentioned above.

Processor 1404 generally represents any type or form of processing unit capable of processing data or interpreting, executing, and/or directing execution of one or more of the instructions, processes, and/or operations described herein. Processor 1404 may direct execution of operations in accordance with one or more applications 1412 or other computer-executable instructions such as may be stored in storage device 1406 or another non-transitory computer-readable medium.

Storage device 1406 may include one or more data storage media, devices, or configurations and may employ any type, form, and combination of data storage media and/or device. For example, storage device 1406 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1406. For example, data representative of one or more executable applications 1412 (which may include, but are not limited to, one or more of the software applications described herein) configured to direct processor 1404 to perform any of the operations described herein may be stored within storage device 1406. In some examples, data may be arranged in one or more databases residing within storage device 1406.

I/O module 1408 may be configured to receive user input and provide user output and may include any hardware, firmware, software, or combination thereof supportive of input and output capabilities. For example, I/O module 1408 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1408 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1408 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1400. For example, one or more applications 1412 residing within storage device 1406 may be configured to direct processor 1404 to perform one or more processes or functions associated with communication facility 302, processing facility 304, fitting facility 306, communication facility 402, current generation facility 404, stimulation facility 406, communication facility 502, empirical electrical spread matrix generation facility 504, and/or modeling facility 506. Likewise, storage facility 308, storage facility 408, and/or storage facility 508 may be implemented by or within storage device 1406.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method of minimizing an effect of channel interaction among a plurality of channels in a multi-channel cochlear implant system, the method comprising:

empirically generating, by a computing device, an electrical spread matrix that is specific to a patient and representative of a channel interaction among a plurality of channels defined by a plurality of electrodes of a multi-channel cochlear implant system associated with the patient;

generating, by the computing device, a model electrical spread matrix that approximates the empirically generated electrical spread matrix and that has a tridiagonal inverse matrix, the model electrical spread matrix based on values of a plurality of longitudinal and transversal resistors representative of current spread through tissue of a cochlea and included in a ladder network model of the cochlea; and using the tridiagonal inverse matrix to determine a set of stimulation current levels to be applied by way of a corresponding set of electrodes included in the plurality of electrodes in order to produce desired stimulation current levels at a plurality of stimulation sites within the cochlea in the presence of the channel interaction;

wherein the using of the tridiagonal inverse matrix to determine the set of stimulation current levels is performed according to the equation $I_r = Z_m^{-1} * (D * I_d)$, wherein $I_r$ represents a matrix of the set of stimulation current levels, $Z_m^{-1}$ represents the tridiagonal inverse matrix, $I_d$ represents a matrix of the desired stimulation current levels, and D represents a diagonal matrix with diagonal values of the empirically generated electrical spread matrix.

2. The method of claim 1, wherein the empirically generating the electrical spread matrix comprises:

successively applying a known stimulation current to each electrode included in the plurality of electrodes; and measuring an intracochlear potential at each of the plurality of electrodes each time the known stimulation current is applied to one of the electrodes.

3. The method of claim 1, wherein the generating of the model electrical spread matrix comprises determining the values of each of the longitudinal and transversal resistors that result in the model electrical spread matrix optimally matching the empirically generated electrical spread matrix.

4. The method of claim 3, wherein the determining of the values of each of the longitudinal and transversal resistors is performed according to the equation $\min_{r_T, r_L} \|Z - Z_m(r_T, r_L)\|_{OFF}$, wherein Z represents the empirically generated electrical spread matrix, $Z_m$ represents the model electrical spread matrix, $r_T$ represents the transversal resistors, and $r_L$ represents the longitudinal resistors of varying order.

5. The method of claim 1, further comprising applying the set of stimulation current levels by way of the corresponding set of the electrode contacts.

6. The method of claim 1, wherein a total number of electrodes included in the set of electrodes is less than a total number of electrodes included in the plurality of electrodes.

7. The method of claim 1, embodied as computer-executable instructions on at least one non-transitory computer-readable medium.

8. A method of minimizing an effect of channel interaction among a plurality of channels in a multi-channel cochlear implant system, the method comprising:

successively applying a known stimulation current to each of a plurality of electrodes disposed within a cochlea of a patient;

measuring an intracochlear potential at each of the electrodes each time the known stimulation current is applied to one of the electrodes;

generating an electrical spread matrix Z based on the measured intracochlear potentials and the known stimulation current;

modeling a current spread through tissues of the cochlea as a ladder network comprising a plurality of segments each including one or more longitudinal resistors representative of current flow between adjacent electrodes and a transversal resistor representative of current that exits the cochlea to return to a reference electrode disposed outside the cochlea;

determining values for each of the longitudinal resistors and each of the transversal resistors that result in a model electrical spread matrix $Z_m$ associated with the ladder network optimally matching the electrical spread matrix Z;

determining a band inverse matrix $Z_m^{-1}$ of the model electrical spread matrix $Z_m$; and determining a required set of stimulation current levels to be applied by way of a corresponding set of the electrodes in order to produce desired stimulation current levels at a plurality of stimulation sites within the cochlea in the presence of the channel interaction according to the equation $I_r = Z_m^{-1} * (D * I_d)$, wherein $I_r$ represents a matrix of the set of required stimulation current levels, $I_d$ represents a matrix of the desired stimulation current levels, and D represents a diagonal matrix of the electrical spread matrix Z.

9. The method of claim 8, further comprising applying the required set of stimulation current levels by way of the corresponding set of the electrodes.

10. The method of claim 8, wherein the determining of the values of each of the longitudinal and transversal resistors is performed according to the equation $\min_{r_T,r_L}\|Z-Z_m(r_T,r_L)\|_{OFF}$, wherein $r_T$ represents the transversal resistors, and $r_L$ represents the longitudinal resistors.

11. The method of claim 8, wherein a total number of electrodes included in the set of electrodes is less than a total number of electrodes included in the plurality of electrodes.

12. The method of claim 8, embodied as computer-executable instructions on at least one non-transitory computer-readable medium.

13. A system for minimizing an effect of channel interaction among a plurality of channels in a multi-channel cochlear implant system, the system comprising:
an implantable cochlear stimulator configured to be implanted within a patient;
a sound processor communicatively coupled to the implantable cochlear stimulator and configured to direct the implantable cochlear stimulator to generate and apply stimulation current to a plurality of stimulation sites within a cochlea of the patient by way of a plurality of electrodes disposed within the cochlea; and
an interface device selectively and communicatively coupled to the sound processor and that
empirically generates an electrical spread matrix that is specific to the patient and representative of a channel interaction among a plurality of channels defined the plurality of electrodes,
generates a model electrical spread matrix that approximates the empirically generated electrical spread matrix and that has a tridiagonal inverse matrix, the model electrical spread matrix based on values of a plurality of longitudinal and transversal resistors representative of current spread through tissue of the cochlea and included in a ladder network model of the cochlea, and
directs the sound processor to use the tridiagonal inverse matrix to determine a set of stimulation current levels to be applied by way of a corresponding set of electrodes included in the plurality of electrodes in order to produce desired stimulation current levels at at least one or more of the stimulation sites in the presence of the channel interaction;
wherein the sound processor uses the tridiagonal inverse matrix to determine the set of stimulation current levels according to the equation $I_r=Z_m^{-1}*(D*I_d)$, wherein $I_r$ represents a matrix of the set of stimulation current levels, $Z_m^{-1}$ represents the tridiagonal inverse matrix, $I_d$ represents a matrix of the desired stimulation current levels, and D represents a diagonal matrix with diagonal values of the empirically generated electrical spread matrix.

14. The system of claim 13, wherein the interface device empirically generates the electrical spread matrix by:
directing the sound processor to direct the implantable cochlear stimulator to successively apply a known stimulation current to each electrode included in the plurality of electrodes; and
directing the sound processor to direct the implantable cochlear stimulator to measure an intracochlear potential at each of the plurality of electrodes each time the known stimulation current is applied to one of the electrodes.

15. The system of claim 13, wherein the interface device generates the model electrical spread matrix comprises by determining the values of each of the longitudinal and transversal resistors that result in the model electrical spread matrix optimally matching the empirically generated electrical spread matrix.

16. The system of claim 15, wherein the interface device is configured to determine the values of each of the longitudinal and transversal resistors in accordance with the equation $\min_{r_T,r_L}\|Z-Z_m(r_T,r_L)\|_{OFF}$, wherein Z represents the empirically generated electrical spread matrix, $Z_m$ represents the model electrical spread matrix, $r_T$ represents the transversal resistors, and $r_L$ represents the longitudinal resistors.

17. The system of claim 13, wherein the implantable cochlear stimulator is configured to apply the set of stimulation current levels by way of the corresponding set of the electrode contacts.

18. The system of claim 13, wherein a total number of electrodes included in the set of electrodes is less than a total number of electrodes included in the plurality of electrodes.

19. A method of minimizing an effect of channel interaction among a plurality of channels in a multi-channel cochlear implant system, the method comprising:
empirically generating, by a computing device, an electrical spread matrix that is specific to a patient and representative of a channel interaction among a plurality of channels defined by a plurality of electrodes of a multi-channel cochlear implant system associated with the patient;
generating, by the computing device, a model electrical spread matrix that approximates the empirically generated electrical spread matrix and that has a tridiagonal inverse matrix, the model electrical spread matrix based on values of a plurality of longitudinal and transversal resistors representative of current spread through tissue of a cochlea and included in a ladder network model of the cochlea; and
using the tridiagonal inverse matrix to determine a set of stimulation current levels to be applied by way of a corresponding set of electrodes included in the plurality of electrodes in order to produce desired stimulation current levels at a plurality of stimulation sites within the cochlea in the presence of the channel interaction;
wherein the generating of the model electrical spread matrix comprises determining, in accordance with the equation $\min_{r_T,r_L}\|Z-Z_m(r_T,r_L)\|_{OFF}$, the values of each of the longitudinal and transversal resistors that result in the model electrical spread matrix optimally matching the empirically generated electrical spread matrix, wherein Z represents the empirically generated electrical spread matrix, $Z_m$ represents the model electrical spread matrix, $r_T$ represents the transversal resistors, and $r_L$ represents the longitudinal resistors of varying order.

* * * * *